United States Patent [19]

Morota et al.

[11] Patent Number: 6,051,425

[45] Date of Patent: Apr. 18, 2000

[54] METHOD FOR PRODUCING TISSUE FORMATION AND TISSUE CULTURE KIT

[75] Inventors: Katsuyasu Morota; Shinichiro Morita, both of Ayabe, Japan

[73] Assignee: Gunze Limited, Kyoto-fu, Japan

[21] Appl. No.: 08/858,905

[22] Filed: May 19, 1997

Related U.S. Application Data

[63] Continuation of application No. 08/529,653, Sep. 18, 1995, abandoned.

[30] Foreign Application Priority Data

Sep. 19, 1994 [JP] Japan .................................. 6-263047

[51] Int. Cl.[7] ....................................................... C12N 5/00
[52] U.S. Cl. ..................... 435/325; 435/347; 435/373; 435/395; 435/397; 435/398; 424/484; 424/488; 428/310.5; 428/316.6
[58] Field of Search .................................. 435/325, 347, 435/373, 395, 397, 398; 428/310.5, 316.6, 321.1; 424/484, 488

[56] References Cited

U.S. PATENT DOCUMENTS

| | | |
|---|---|---|
| 4,485,096 | 11/1984 | Bell . |
| 4,835,102 | 5/1989 | Bell et al. . |
| 4,841,962 | 6/1989 | Berg et al. ................................ 128/56 |
| 5,024,841 | 6/1991 | Chu et al. ................................ 424/422 |
| 5,350,583 | 9/1994 | Yoshizato et al. ...................... 424/484 |

FOREIGN PATENT DOCUMENTS

91/16010  10/1991  WIPO .

OTHER PUBLICATIONS

"Composite Skin Substitute Composed of Cultured Keratinocytes and Fibroblasts Combined in Collagen Matrix" Ohtake et al., J. Jpn. P.R.S., 10: 165–180, 1990.

"Characterization of a Three Dimensional Co–Culture of Neonatal Human Fibroblasts and Keratinocytes" Slivka, et al. The Journal of Investigative Dermatology, 96: 544A, 1991.

*Primary Examiner*—Leon B. Lankford, Jr.
*Attorney, Agent, or Firm*—Knobbe, Martens, Olson & Bear, LLP

[57] ABSTRACT

A matrix for tissue culture comprising two kinds of sponges having at least one different physical property and/or at least one different chemical property; a method for culturing tissue using said matrix for tissue culture comprising inoculating and culturing first cell on a first sponge, laminating a second sponge thereon, and inoculating and culturing second cell on said second sponge; a method for fixing a cultured tissue comprising placing a cultured tissue in gelatin solution solated by elevating temperature, lowering temperature to gelatinize gelatin to fix the cultured tissue by said gelatinated gelatin; and an artificial skin fixed comprising dermis layer fixed by gelatin and epidermis layer laminated on the dermis layer.

15 Claims, 2 Drawing Sheets

METHOD FOR PRODUCING TISSUE FORMATION AND TISSUE CULTURE KIT

RELATED APPLICATION

The present application is a continuation application of application Ser. No. 08/529,653, filed Sep. 18, 1995, now abandoned.

FIELD OF THE INVENTION

The present invention relates to a matrix for tissue culture, a method for culturing tissue, a method for fixing cultured tissue and an artificial skin fixed.

BACKGROUND OF THE INVENTION

In the field of medicine, food, cosmetics, etc., a number of products has been developed and sold in every year. In order to develop such products directly applied to a human body, confirmation of safety thereof is essential. An animal testing mainly conducted as a safety check test has drawbacks in expense, long test period and incomplete equivalence to human. In addition, improvement of an animal testing is demanded from the viewpoint of prevention of cruelty to animals.

A method for measuring an intensity of response by candidate substances comprising applying a tissues-specific substance to a tissue model reconstructed in vitro with cells or substances of said tissue is recently attempted as one of alternatives.

On the other hand, conventional artificial organs composed of plastics and metals as raw material, artificial organs further combined with materials from organism and so-called hybrid-type artificial organs further combined with cultured cells have been developed in a clinical field.

A cultured skin is a comparatively well-developed example in the field of tissue models and artificial organs. A cultured skin includes skin prepared by culturing human fibroblast in collagen gel, followed by inoculating and culturing human keratinocyte on the gel when the gel is shrunk (U.S. Pat. No. 4,485,096); skin prepared by inoculating and culturing human fibroblast on nylon mesh, followed by inoculating and culturing human keratinocyte thereon when pores of the mesh is filled up with secreted materials from fibroblast (Slivka, S. R., L. Landeen, Zimber, M., G. K. Naughton and R. L. Bartel, J. Invest. Dermatol., 96: 544A, 1991); and skin prepared by inoculating and culturing human fibroblast in collagen sponge, followed by laminating collagen gel or film inoculating and culturing human keratinocyte thereon (J. Jpn. P. R. S., 10, 165–180 (1990); Japanese Examined Patent Publication No. 47043/1995).

The most important problem in producing tissue models, typically cultured skins, and artificial organs is to reconstruct a three-dimensional structure of tissues or organs as quickly as possible. For example, a skin mainly comprises keratinocyte in epidermis, fibroblast in dermis and inter-cellular substances such as collagen, which are not existed in a mixed form. A skin comprises a dermis layer formed by three-dimensional proliferation of fibroblast in collagen fiber matrix and an epidermal layer formed thereon by laminating keratinocyte over and over again in a complex differentiation manner from basal layer to corneous layer by way of several steps.

However, conventional tissue models and artificial organs do not have a desired three-dimensional structure and have a problem that in spite of progress of development with respect to a cultured skin, in particular, it takes more than one month to prepare a conventional cultured skin from inoculation of cells to completion of skin reconstruction, and that keratinocyte laminates in only several layers and is low in differentiation stage in comparison with an actual human skin.

In order to overcome the problems mentioned above, it is an object of the invention to provide a matrix for tissue culture and a method for culturing tissue which make it possible to obtain tissue culture having a desired three-dimensional structure within a short period of time by culturing heterogenous or homogenous cells individually or simultaneously in suitable conditions thereof.

It is another object of the invention to provide a method for fixing cultured tissue and artificial skin fixed, suitable for preservation and transportation, which inhibit spill of liquid from container thereof and destruction of cultured tissue (especially cultured skin) when vibrating and upsetting container thereof.

DISCLOSURE OF THE INVENTION

Figure 1:
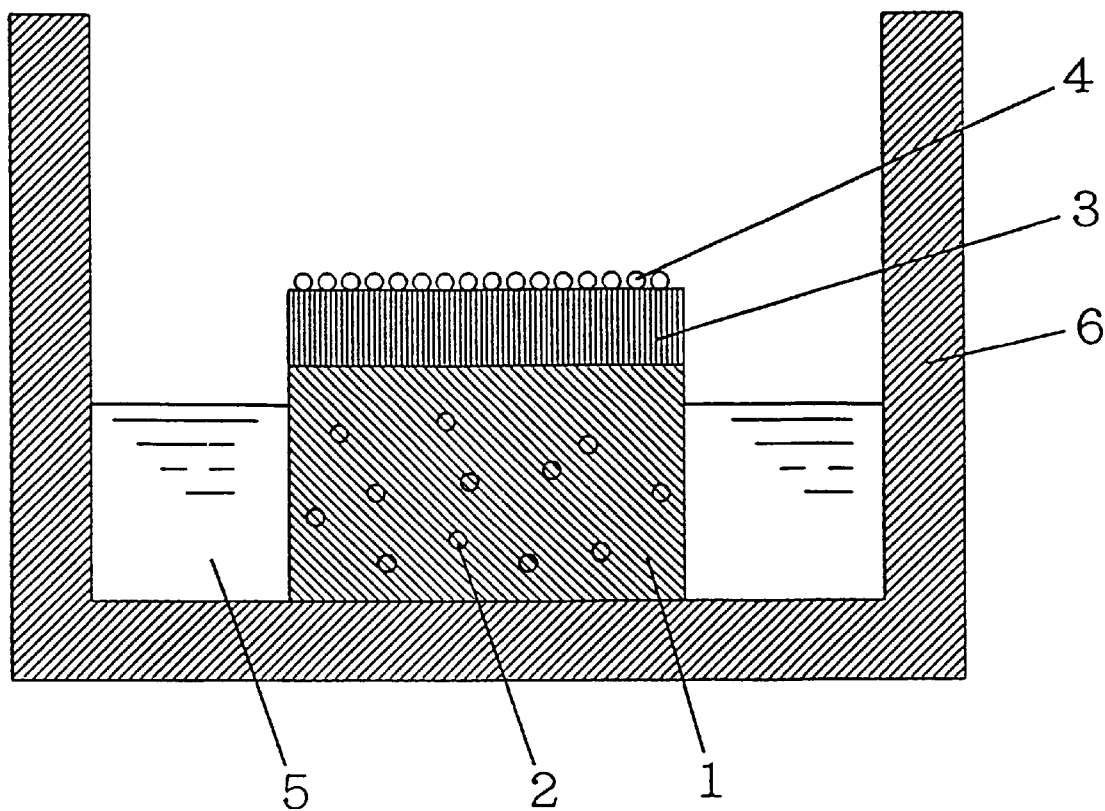
FIG. 1 is a sectional view typically showing culture conditions.

Thus, the invention provides a matrix for tissue culture, a method for culturing tissue, a method for fixing a cultured tissue and an artificial skin fixed as shown below;

Item 1. A matrix for tissue culture comprising a first sponge and a second sponge having at least one different physical property and/or at least one different chemical property.

Item 2. A matrix for tissue culture according to item 1 wherein said physical property is pore size.

Item 3. A matrix for tissue culture according to item 1 wherein said chemical property is degree of crosslinking.

Item 4. A matrix for tissue culture according to item 1 wherein said sponge is made of bio-compatible polymer.

Item 5. A matrix for tissue culture according to item 1 wherein said bio-compatible polymer is collagen.

Item 6. A method for culturing tissue using a matrix for tissue culture comprising a first sponge and a second sponge having at least one different physical property and/or at least one different chemical property, which comprises inoculating and culturing first cell on said first sponge, laminating said second sponge thereon, and inoculating and culturing second cell on said second sponge.

Item 7. A method for culturing tissue according to item 6 wherein said first cell is different from said second cell.

Item 8. A method for culturing tissue according to item 7 wherein said first cell is fibroblast and said second cell is keratinocyte.

Item 9. A method for culturing tissue according to item 6 wherein said second sponge is degraded and disappeared in a culture process.

Item 10. A method for fixing a cultured tissue comprising placing the cultured tissue in gelatin solution solated by elevating temperature, lowering temperature to gelatinize gelatin to fix the cultured tissue by said gelatinated gelatin.

Item 11. A method for fixing a cultured tissue according to item 10 wherein said cultured tissue is a cultured skin.

Item 12. A method for fixing a cultured tissue according to item 10 wherein said gelatin solution is prepared by dissolving gelatin in tissue culture medium.

Item 13. A method for fixing a cultured tissue according to item 11 wherein said cultured skin has a two-layer structure of epidermis and dermis, said epidermis contacting with gas phase and said dermis being placed in a gelatin solution to fix said cultured skin by gelatinized gelatin.

Item 14. An artificial skin fixed comprising a dermis layer fixed by gelatin and an epidermis layer laminated on the dermis layer.

I. Items 1–9

Said first and second sponges employed according to the invention have a porous structure. Said physical property includes pore size. In case of inoculation of the first cell on the first sponge as a matrix for tissue culture, first cell is dropped into first sponge and proliferate three-dimensionally within said porous structure when said porous structure is sufficiently larger than size of first cell. In contrast, second cell remain on second sponge when pore of second sponge is smaller than size of cells. Thus, combination of (i) first and second sponges having a different physical property, such as pore size and (ii) first and second cells facilitates not only individual culture of a variety of cells, but also control of proliferating state thereof.

Materials of said sponges include biocompatible polymer, such as type-I, -II, -III and -IV collagens, gelatine, sodium alginate, fibronectin, laminin, hyaluronic acid, chitin, chitosan, EHS mouse tumour solubilized extract, etc., preferably include type-I, -II, -III and -IV collagens.

A variety of methods for preparing said sponges have been disclosed. One of said method disclosed in Japanese Unexamined Patent Publication No 43734/1993 comprises adding lipophilic organic solvent to a collagen solution, homogenizing said solution to expand, and then lyophilizing the homogenate. According to this method, collagen sponge having uniform pore size may be obtained.

The other methods previously reported may be employed to produce sponges of the invention.

Said chemical property includes degree of crosslinking. When collagen is employed as bio-compatible polymer, the collagen sponge may be degraded and disappeared by the action of collagenase secreted by cells.

However, resistance to collagenase may be imparted by introducing crosslinking to collagen sponge. An intensity of resistance thereof may be controlled by degree of crosslinking. When culture of first and second cells is carried out by employing the matrix for tissue culture provided with first and second collagen sponges having different pore size, high degree of crosslinking is introduced into first collagen sponge, and low degree of crosslinking is introduced into second collagen sponge, to make sure that only second collagen sponge may be selectively degraded and disappeared. Further, when crosslinking conditions of low crosslinked collagen sponge are suitably selected, second collagen sponge with desired rate of disappearance may be obtained.

Introduction of crosslinking into said sponge of the invention may be carried out, for example, by heat-dehydration crosslinking, chemical crosslinking, etc. Crosslinking agents for chemical crosslinking is not specifically limited to, but include glutaraldehyde, formaldehyde and like aldehydes; hexamethylene diisocyanate, tolylene diisocyanate, and like diisocyanates; ethyleneglycol diglycidylether, and like epoxides; and carbodiimide hydrochlorides etc., preferably include glutaraldehyde.

As shown above, the matrix for tissue culture having desired structure may be obtained by suitable combination of first and second sponges having at least one different physical property and/or at least one different chemical property.

The invention is described below in detail taking a method of preparation of human skin model as an embodiment.

A first sponge having a pore size of 50 $\mu$m or more, preferably 80–95 $\mu$m, and a thickness of 1–5 mm is prepared, and then chemical crosslinking is introduced into the sponge.

When human fibroblast in dermis is inoculated on first sponge, the fibroblast drops into the first sponge and proliferates three-dimensionally within pores of the sponge. The first sponge is not degraded and disappeared because of tight crosslinking introduced into the first sponge.

The second sponge loosely crosslinked having a pore size of 1–30 $\mu$m, preferably 5–20 $\mu$m and a thickness of 1–2 mm is laminated thereon. Human keratinocyte in epidermis is inoculated on second sponge. The keratinocyte proliferates on the surface of the second sponge.

Although it depends on kind of second cell inoculated on the second sponge, when the pore size of second sponge into which crosslinking is introduced is lower than 1 $\mu$m, water or nutrient components may not be passed through the second sponge freely, leading to insufficient supply of nutrient to the second cell placed on the second sponge, thereby undesirable. In addition, when the pore size is more than 30 $\mu$m, second cell may not be fixed on the second sponge. A loose-crosslinking introduced into second sponge by heat-dehydration crosslinking under the conditions of 105° C. and 24 hours is degraded and disappeared within five days during culture in DME medium containing 5% serum.

As shown above, the loose-crosslinked second sponge exerts effects on not only preventing human keratinocyte from dropping thereto, i.e., giving scaffold to human keratinocyte, but also, because of loose crosslinking, degradation and disappearance of the second sponge after giving scaffold to human keratinocyte inoculated and proliferated on the second sponge.

The disappearance of the second sponge inexisting in actual skin makes the resulting skin model nearer to the actual skin.

The first and second cells employed according to the method for culturing tissue of the invention are not limited to human fibroblast and human keratinocyte but include other animal cells.

II. Items 10–14

Since cultured tissue, preferably skin, is fixed and held with surrounding jelly-like gelatine by immersing the tissue in solated gelatine, followed by gelatinizing the gelatine, the tissue is not moved or separated from surrounding gelatine, even when tissue-fixing gelatin in a container is vibrated, fallen sidelong or overturned. Further, gelatin is not spilled from a container because of high-viscosity thereof. Therefore, the cultured tissue, especially skin, fixed is free of troubles during transportation.

Employing cell culture medium as a solvent of gelatin facilitates sufficient supply of nutrients required and stable cell conditions in a long period of time without death and deterioration of cells. Cultured skin having a two-layer structure of epidermis and dermis introduces a problem, such as swelling and death of cell, when epidermis does not contact with atmosphere and when dermis does not contact with nutrient supply, i.e., culture medium. In contrast, the method for fixing cultured tissue, especially skin, of the invention does not introduce such problems.

Gelatin employed according to the invention is not specifically limited to, but prepared by extraction from skin, sinew, body, fascia, etc. of aminals such as pig, cattle, etc., and has a sol-gel transition point of 20–35° C. Therefore, glue may be employed as gelatin.

The concentration of gelatin in solvent ranges from 1 to 20% by weight, preferably 5 to 10% by weight in view of sol viscosity, gelatinizing time, gel strength formed. When gelatin concentration is too high, a problem of cell damage during operation of fixation and removal arises. When gelatin concentration is too low, a problem of too long gelatinizing time and inferior maintenance arises.

As a solvent, DME medium containing 5% serum is preferable so as to supply sufficient nutrients during preservation and transportation.

A preferable cultured skin applicable to the invention is not specifically limited to, but includes a double-layered artificial skin for toxicity test or treatment of wound, prepared by inoculating and proliferating fibroblast on a collagen sponge, followed by inoculating and proliferating keratinocyte, and a single-layered artificial skin.

Integration of cultured tissue with gelatin gel may be carried out by adding heat-solated gelatin in an suitable amount to a container with cap, placing cultured tissue in the gelatin at the center of the container and then cooling the container to gelation temperature to fix the tissue.

Said integration may also be carried out by placing a cultured tissue at the center of a container, pouring a required amount of solated gelatin into the container and then cooling the container to gelation temperature to fix the tissue. Subsequently, the fixed tissue is maintained at 10° C. or higher temperature so as not to separate cells, or, below 37° C. for prevention of cell death. When taking out the fixed skin, the skin may be directly taken out from the gelated gelatin, but preferably the container is heated to solate gelatin to inhibit cell damage. When agarose as a gel is employed in place of gelatine, dipping cells in solated agarose will cause cell death because agarose is solated at as high as 60–70° C. which is higher than viable temperature of cells, i.e., about 40° C. Gelatin adhered to the cultured tissue is preferably washed with saline.

The invention will be described below in detail.

BEST MODE FOR CARRYING OUT THE INVENTION

EXAMPLE 1

Preparation of Cultured Skin (1) Preparation of Tight-crosslinked Sponge

Chloroform (0.5 g) was added to 3 mg/ml concentration of Type I collagen solution (50 g), and the mixture was homogenized with homogenizer at 6,000 rpm for 1 minute. The homogenate was poured into frame made of stainless steel, frozen at −40° C., subsequently lyophilized at 30° C. for 24 hours under vacuum (0.01 mmHg). After heat-dehydration for crosslinking at 105° C. for 24 hours under vacuum (0.01 mmHg), chemical crosslinking was introduced to the sponge by immersing the sponge in a 0.2% glutaraldehyde solution for 24 hours. The resulting sponge was dried by lyophilization to give tight-crosslinked collagen sponge having a pore size of 90 $\mu$m and a thickness of 3 mm.

(2) Preparation of Loose-crosslinked Sponge

A 0.3% of Type I collagen aqueous solution (pH 3) was diluted with ethanol to give aqueous solution containing 0.285% of collagen and 10% of ethanol. A 10 g portion of the solution was poured into Schale (diameter: 9 cm), which was frozen at −135° C., lyophilized at 40° C. for 24 hours under 0.1 degree of vacuum. The resulting sponge was further heat-dehydrated for crosslinking at 105° C. for 24 hours under vacuum (0.01 mmHg) to give loose-crosslinked collagen sponge having a pore size of 30 $\mu$m and a thickness of 1 mm.

(3) Inoculation and Culture of Cells

The tight-crosslinked collagen sponge prepared in step (1) was spread on the surface of a 24-well plate for culture, a suspension of human fibroblast (product of KURABO Industries Ltd.) in MEM medium containing 10% serum was inoculated on the sponge at a concentration of $5.0 \times 10^5$ cells/cm$^2$ and then cultured overnight at 37° C. for under 5% $CO_2$ until cells were completely adhered. The loose-crosslinked collagen sponge prepared in step (2) was laminated thereon, a suspension of human keratinocyte (product of KURABO Industries Ltd.) in KGM medium was inoculated at a concentration of $5.0 \times 10^5$ cells/cm$^2$ and then cultured overnight at 37° C. under 5% $CO_2$ until cells were completely adhered.

The culture matrix was taken out from the 24-well plate for culture and placed on 6-well plate for culture, where DME medium containing 5% serum was employed in place of KGM medium. Further continuing culture for five days while contacting human keratinocyte with air by adjusting a volume of culture medium to give a desired cultured skin.

Said tight-crosslinked collagen sponge and loose-crosslinked collagen sponge mean crosslinked collagen sponge to a high degree and crosslinked collagen sponge to a low degree.

FIG. 1 demonstrates a culture condition typically. In FIG. 1, 1 is tight-crosslinked collagen sponge; 2 is human fibroblast; 3 is loose-crosslinked collagen sponge; 4 is human keratinocyte; 5 is medium; and 6 is plate for culture.

Figure 2:
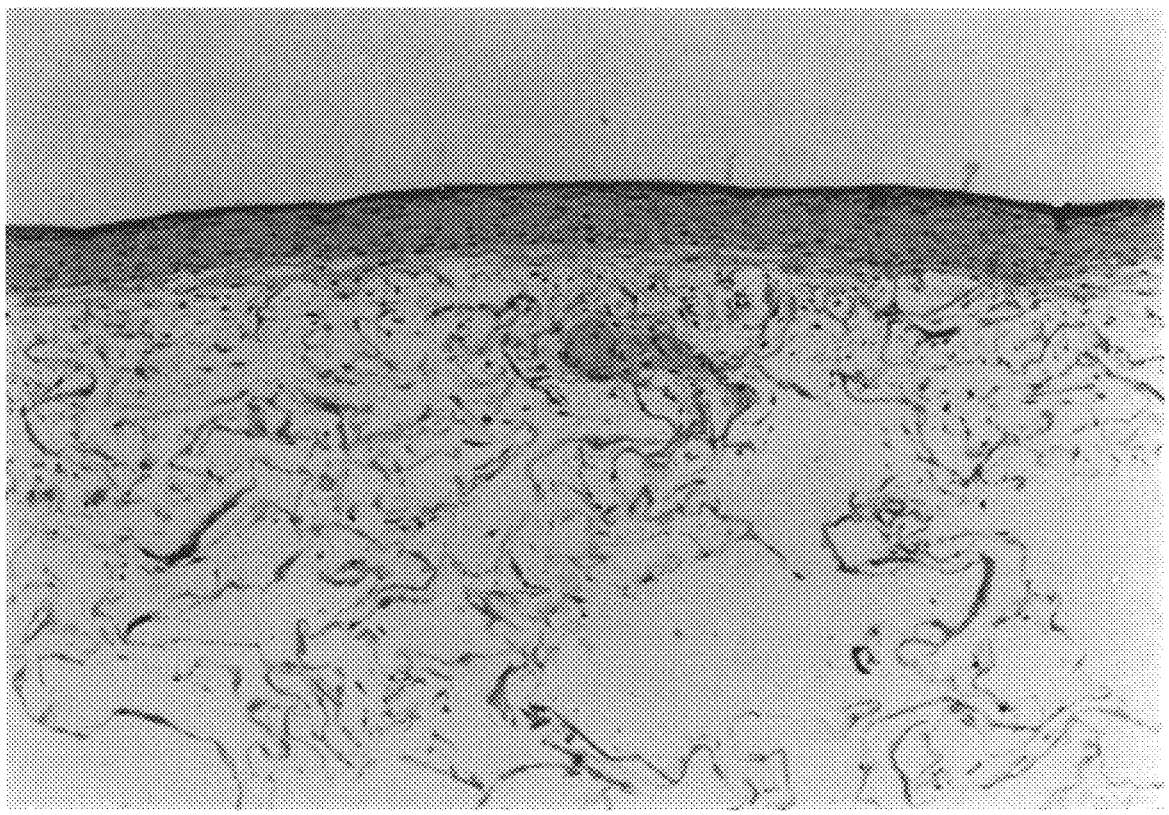
FIG. 2 shows a photograph of an artificial skin of the invention.

The cultured skin thus obtained was subjected to formalin fixation and then HE staining. Observation of the skin obtained clearly demonstrates that human fibroblast 2 proliferated well three-dimensionally in tight-crosslinked collagen sponge 1. The photograph of artificial skin of the invention after HE staining is shown in FIG. 2.

After starting air-liquid interface culture, loose-crosslinked collagen sponge 3 was almost disappeared and human keratinocyte was laminated in a several layers on day 1. Differentiation of human keratinocyte was started on day 3. On day 5, well-differentiated epidermis having 10 layers similar to human skin was obtained.

As stated above, cultured tissue with desired three-dimensional structure, in particular, cultured skin reproducing human skin structure was obtained artificially and quickly by culturing heterogenous or homogenous cells separately or simultaneously in suitable conditions of each cells. Therefore, the cultured tissue of the invention is suitable for safety test in terms of toxicity, irritation, permeability of medicine, cosmetics, etc., and is also applicable to treatment of burn losing epidermis and dermis layer.

EXAMPLE 2

I. Fixation of Skin Model by Gelatin (1) Preparation of Gelatin Solution

DME medium containing 5% serum (100 ml) as a solvent was maintained at 37° C. To the solution was added gelatin powder (10 g) from bovine bone sterilized by EOG, and the mixture was stirred to dissolve the gelatin powder. The gelatin solution was free-flowing and low viscosity solution like water.

(2) Fixation by Gel

The skin model obtained in example 1(3) having double-layer structure of dermis and epidermis was placed at the center of 6-well plate. The gelatin sol (3 ml) prepared in example 2(1) was added around the model. When using this liquid volume, surface epidermis layer was contacted with gas phase, i.e., air, and dermis layer was then immersed in gelatin solution. This plate was allowed to stand at room temperature (about 20° C.) for 30 minutes leading to fixation of said skin model by jelly-like gelatin with high viscosity.

II. Check Test Under Preservation and Transportation

In order to check stability of the cultured skin model thus fixed under preservation and transportation conditions, the number of normal cells of the skin model of the invention after allowing the model to stand at room temperature (20° C.) for 3 and 5 days was counted by neutral red method. The skin model before fixation cultured at 37° C. was employed as control. The determined values, i.e., 97.7% (after 1 day), 101.8% (after 3 days), 102.0% (after 5 days) were obtained provided that the determined value of control was regarded as 100%.

At the same time, observation of tissue slice of the model of the invention on day 5 demonstrates that cells had substantially no change with respect to structure thereof. Further, cultured skin fixed with gelatin gel maintained original conditions and was free of separation and damage.

As shown in example 2, the skin model of the invention is free of problems such as damage or deterioration of cells during transportation or handling, since the cultured skin was fixed and maintained by high-viscosity gelatin using characteristics of reversible transformation thereof between sol and gel within a range of 20 to 35° C.

The cultured tissue of the invention was characterized in that cell culture medium may be employed as solvent, that growing conditions of tissue may be maintained by adding suitable nutrients, and that cells are not damaged or died within a sol-gel transformation temperature. Therefore, the cultured tissue fixed is suitable for preservation until use and during transportation. Further, when using bottom-free container, workability is improved and damage is decreased in taking out and moving operation of cultured tissue fixed. In case that gelatin solution itself is employed as cell culture medium, cultured tissue is not necessary to move resulting in improvement of workability and minimize damage during shifting operation.

We claim:

1. A method for producing a tissue formation having a structure differentiated in relation to depth, comprising the steps of:

inoculating a first culturing cell on a first bio-compatible sponge having first pores, said first pores having a size such that said first culturing cell is accommodated in said first pores to allow said first culturing cell to proliferate inside said first bio-compatible sponge;

inoculating a second culturing cell on a second bio-compatible sponge having second pores, said second pores having a size such that said second culturing cell is accommodated on said second bio-compatible sponge where inoculated to allow said second culturing cell to proliferate on said second bio-compatible sponge, said second bio-compatible sponge having a lower degree of resistance against collagenase secreted by said second culturing cell than that of said first bio-compatible sponge against said first culturing cell; and culturing said first and second culturing cells using at least one culture medium to produce a tissue formation having a structure differentiated in relation to depth.

2. A method according to claim 1, wherein said first bio-compatible sponge is chemically crosslinked to a degree sufficient to prevent decomposition during culture of the cell, and said second bio-compatible sponge is crosslinked by heat-dehydration to a degree sufficient for said second bio-compatible sponge to decompose and dissipate at the conclusion of culture of the cell.

3. A method according to claim 1, wherein said first bio-compatible sponge and said bio-compatible second sponge are each made of a bio-compatible polymer selected from the group consisting of type-I, -II, -III, and -IV collagens, gelatine, sodium alginate, fibronectin, laminin, hyaluronic acid, chitin, chitosan, and EHS mouse tumor solubilized extract.

4. A method according to claim 1, wherein said bio-compatible polymer is type-I, II, -III, or -IV collagen.

5. A method according to claim 1, wherein the pore size of said first pores is 50 $\mu$m or more, and the pore size of said second pores is 1–30 $\mu$m.

6. A method according to claim 1, wherein said first culturing cell is a human fibroblast cell, and said second culturing cell is a human keratinocyte cell.

7. A tissue culture kit for producing a tissue formation having a structure differentiated in relation to depth, comprising:

a first culturing cell;

a second culturing cell;

a first bio-compatible sponge having first pores, on which said first culturing cell is inoculated, said first pores having a size such that said first culturing cell is accommodated in said first pores to allow said first culturing cell to proliferate inside said first bio-compatible sponge;

a second bio-compatible sponge having second pores, on which said second culturing cell is inoculated, said second pores having a size such that said second culturing cell is accommodated on said second bio-compatible sponge where inoculated to allow said second culturing cell to proliferate on said second bio-compatible sponge, said second bio-compatible sponge having a lower degree of resistance against collagenase secreted by said second culturing cell than that of said first bio-compatible sponge against said first culturing cell; and at least one culture medium for culturing said first cell and second cell.

8. A tissue culture kit according to claim 7, wherein said first bio-compatible sponge is chemically crosslinked to a degree sufficient to prevent decomposition during culture of the cell, and said second bio-compatible sponge is crosslinked by heat-dehydration to a degree sufficient for said second bio-compatible sponge to decompose and dissipate at the conclusion of culture of the cell.

9. A tissue culture kit according to claim 7, wherein said first bio-compatible sponge and said bio-compatible second sponge are each made of a bio-compatible polymer selected from the group consisting of type-I, -II, -III, and -IV collagens, gelatine, sodium alginate, fibronectin, laminin, hyaluronic acid, chitin, chitosan, and EHS mouse tumor solubilized extract.

10. A tissue culture kit according to claim 9, wherein said bio-compatible polymer is type-I, -II, -III, or -IV collagen.

11. A tissue culture kit according to claim 9, wherein the pore size of said first pores is 50 $\mu$m or more, and the pore size of said second pores is 1–30 $\mu$m.

12. A tissue culture kit according to claim 9, wherein said first culturing cell is a human fibroblast cell, and said second culturing cell is a human keratinocyte cell.

13. A tissue culture kit for a tissue formation having a structure differentiated in relation to depth, comprising a bio-compatible matrix essentially consisting of:

a first bio-compatible sponge adapted to be inoculated with a first culturing cell, said first bio-compatible sponge having a thickness of 1–5 mm and having first pores having a size of at least 50 $\mu$m such that the first culturing cell is accommodated in the first pores, said first bio-compatible sponge being chemically crosslinked to a degree sufficient to prevent decomposition during culture of the cell; and a second bio-compatible sponge adapted to be inoculated with a second culturing cell, said second bio-compatible sponge having a thickness of 1–2 mm and having second pores having a size of 1–30 $\mu$m such that the second culturing cell is accommodated on said second bio-compatible sponge where inoculated, said second bio-compatible sponge being crosslinked by heat-dehydration to a degree sufficient for said second bio-compatible sponge to decompose and dissipate at the conclusion of culture of the cell.

14. A tissue culture kit according to claim 13, wherein said first bio-compatible sponge and said second bio-compatible sponge are made of collagen.

15. A tissue culture kit according to claim 13, wherein said bio-compatible sponge matrix consists of said first bio-compatible sponge and said second bio-compatible sponge.

* * * * *